United States Patent
Lin et al.

(10) Patent No.: US 8,983,533 B2
(45) Date of Patent: *Mar. 17, 2015

(54) MULTIMODE COMMUNICATION TERMINAL AND MULTIMODE COMMUNICATION IMPLEMENTATION

(75) Inventors: Yong Hua Lin, Beijing (CN); Hong Hua Song, Beijing (CN); Yu Dong Yang, Beijing (CN); Yu Yuan, Beijing (CN); You Zhou, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 303 days.

This patent is subject to a terminal disclaimer.

(21) Appl. No.: 13/462,313

(22) Filed: May 2, 2012

(65) Prior Publication Data

US 2012/0287870 A1 Nov. 15, 2012

Related U.S. Application Data

(63) Continuation of application No. 12/466,985, filed as application No. PCT/EP2007/059888 on Sep. 19, 2007, now Pat. No. 8,195,225.

(30) Foreign Application Priority Data

Oct. 24, 2006 (CN) .......................... 2006 1 0137161

(51) Int. Cl.
*H04M 1/00* (2006.01)
*G01N 3/24* (2006.01)
*G01N 19/04* (2006.01)

(52) U.S. Cl.
CPC .................. *G01N 3/24* (2013.01); *G01N 19/04* (2013.01); *G01N 2203/0025* (2013.01); *G01N 2203/021* (2013.01); *G01N 2203/0623* (2013.01)
USPC .... 455/553.1; 455/168.1; 455/73; 455/552.1; 455/78; 455/450; 370/335; 370/342; 370/208

(58) Field of Classification Search
None
See application file for complete search history.

(56) References Cited

U.S. PATENT DOCUMENTS 5,507,035 A 4/1996 Bantz et al.
7,133,646 B1 11/2006 Miao
(Continued)

FOREIGN PATENT DOCUMENTS

CN 200610137161 10/2006
EP 1703675 A1 9/2006
(Continued)

OTHER PUBLICATIONS

Korean Patent Abstract for Publication No: 1020060022630A; Published: Mar. 10, 2006; Applicant Samsung Electronics, Co.; 1 page.
(Continued)

*Primary Examiner* — Kent Chang
*Assistant Examiner* — Benjamin Morales Fernandez
(74) *Attorney, Agent, or Firm* — Cantor Colburn LLP

(57) ABSTRACT

A method for enabling a MIMO operation mode in a multimode communication terminal includes switching a first channel module to have parameter characteristics consistent with those of a second channel module, so that the multimode communication terminal enables the MIMO operation mode by using the first channel module and the second channel module at the same time. The method also includes extracting corresponding parameters from the second channel module and configuring the first channel module to be switched with the extracted parameters, such that the first channel module and second channel module enable the multimode communication terminal to perform MIMO communication. The method further includes issuing, upon determination of a switch, notification instructions to means in channel switch layer means and changing a data channel associated with the first channel module, such that the first channel module and second channel module can be adapted to the MIMO operation mode.

16 Claims, 10 Drawing Sheets

(56) References Cited

U.S. PATENT DOCUMENTS

| | | |
|---|---|---|
| 7,251,499 B2 | 7/2007 | Ella et al. |
| 7,280,810 B2 | 10/2007 | Feher |
| 7,403,508 B1 | 7/2008 | Miao |
| 2003/0228857 A1 | 12/2003 | Maeki |
| 2004/0185899 A1* | 9/2004 | Hayem et al. ............ 455/552.1 |
| 2004/0204035 A1 | 10/2004 | Raghuram et al. |
| 2005/0085201 A1 | 4/2005 | Martin et al. |
| 2005/0250468 A1 | 11/2005 | Lu et al. |
| 2006/0022889 A1 | 2/2006 | Chiang et al. |
| 2006/0022890 A1 | 2/2006 | Chiang et al. |
| 2006/0056316 A1 | 3/2006 | Chandra et al. |
| 2006/0056345 A1 | 3/2006 | Marinier et al. |
| 2006/0074641 A1 | 4/2006 | Goudar et al. |
| 2006/0079220 A1 | 4/2006 | Cha et al. |
| 2006/0189277 A1 | 8/2006 | Ranta et al. |
| 2006/0292986 A1* | 12/2006 | Bitran et al. ............. 455/41.2 |

FOREIGN PATENT DOCUMENTS

| | | |
|---|---|---|
| JP | 2001-345778 | 12/2001 |
| JP | 2005295516 | 10/2005 |
| KR | 1020060022630 | 10/2006 |
| WO | 2005039063 A1 | 4/2005 |
| WO | 2005069846 A2 | 8/2005 |
| WO | 2005122414 A1 | 12/2005 |
| WO | 2008049700 A1 | 5/2008 |

OTHER PUBLICATIONS

Patent Abstract of Japan for Publication No. 2001-345778; Published Dec. 14, 2001; Applicant: Sony Corp.; 1 page.

Patent Abstract of Japan for Publication No. 2005-295516; Date of Publication Oct. 20, 2005; Applicant: Matsushita Electric Ind. Co. Ltd.; 1 page.

Eul, Hermann "ISSCC 2006/ Feb. 6, 2006 / 10:15 a.m."; 1.2 ICs for Mobile Multimedia Communications, 2006 IEEE International Solid-State Circuits Conference 1-4244-0079-1/06 2006 IEEE; 19 pages.

Notice of Allowance for U.S. Appl. No. 12/446,985, filed Jan. 4, 2012; First Named Inventor: Yong Hua Lin; 2617; Mailing Date: Feb. 3, 2012.

Office Action for U.S. Appl. No. 12/446,985, filed Jan. 4, 2010; First Named Inventor: Yong Hua Lin; 2617; Mailing Date: Oct. 14, 2011.

Said, Salim Y., et al. "Wireless Generations: Transitions and Multimedia Suitability" Electrical and Computer Engineering, Canadian Conference, IEEE, P1, May 2006; pp. 1805-1808.

\* cited by examiner

MULTIMODE COMMUNICATION TERMINAL AND MULTIMODE COMMUNICATION IMPLEMENTATION

CROSS REFERENCE TO RELATED APPLICATIONS

The present application is a continuation of U.S. patent application Ser. No. 12/466,985 filed on Jan. 4, 2010 which is a National Stage of International Application No. PCT/EP2007059888 filed on Sep. 19, 2007 which claims priority to Chinese Patent Document No. 200610137161.0 filed on Oct. 24, 2006, the disclosure of which is herein incorporated by reference.

BACKGROUND

The present invention generally relates to wireless or mobile communication, and more particularly, to a multimode wireless communication terminal enabling an antenna array and a corresponding multimode communication implementation method.

In the wireless mobile communication terminal market with fierce competition, terminal manufacturers are committed to developing wireless mobile communication terminals comprising a plurality of wireless interfaces. These wireless interfaces establish wireless connections for example based on the Bluetooth wireless technique, the WLAN (wireless local area network) protocol, 2G (the 2nd generation network, like GSM—Global System for Mobile Communication), 2.5G (the 2.5-generation system, like GPRS—General Packet Radio Service), 3G (the 3rd generation system, like UMTS—Universal Mobile Telecommunication System) and the next generation data transfer protocol such as WiMax/Wibro and the like.

FIG. 1A depicts an exemplary configuration diagram of a multimode communication terminal in the prior art. The communication terminal 100A comprises three wireless interfaces, namely a Bluetooth interface 1100 dedicated to data communication based on the Bluetooth wireless technique, a WLAN interface 1200 dedicated to data communication according to the WLAN protocol, and a mobile communication interface 1300 dedicated to data communication according to the mobile communication protocol (e.g. GSM, GPRS, CDMA, etc.). Each of the interfaces comprises a baseband processor adapted to its own used protocol (i.e. comprising a Bluetooth baseband processor 1110, a WLAN baseband processor 1210 and a mobile communication baseband processor 1310, respectively), a clock module for providing a sample clock according to its own used protocol (i.e. comprising a Bluetooth clock 1120, a WLAN clock 1220 and a mobile communication clock 1320, respectively), an A/D and D/A converter for converting a signal from analog to digital and from digital to analog according to its respective clock signals (i.e. comprising an A/D and D/A converter 1130, an A/D and D/A converter 1230 and an A/D and D/A converter 1330, respectively), a RF processing module adapted to its own used protocol (i.e. comprising a Bluetooth RF processing module 1140, a WLAN RF processing module 1240 and a mobile communication RF processing module 1340, respectively), and an antenna adapted to the used protocol (i.e. comprising a Bluetooth antenna 1150, a WLAN antenna 1250 and a mobile communication antenna 1350, respectively). Due to the similarity in performed functions, the A/D and D/A converters, the RF processing modules and the antennas at respective wireless interfaces usually have similar or even the same physical structure. The difference is that depending on respective used protocols, they operate in different modes and accordingly have different operation characteristic parameters, such as RF central frequency, bandwidth, IF central frequency, baseband sample rate etc. As an example, FIG. 1 schematically depicts the main configuration of the RF processing modules at respective interfaces. They have the same configuration but operate on different frequency bands. For example, Bluetooth RF processing module 1140 operates on 2.402-2.408 GHz, whereas mobile communication RF processing module 1340 using CDMA2000-1x operates on 1.6 GHz. The configuration and operating principle of such RF processing modules are well known to those skilled in the art, and the detailed description thereof is omitted here.

According to the multimode communication terminal of the structure as depicted in FIG. 1, signals are independently received/transmitted and baseband processed via respective interfaces, and data to be received or transmitted is independently exchanged with an application processor 1000 which can start/cease the operation of one or more wireless interfaces according to user's commands or predetermined conditions.

To support higher-speed multimedia application, such as Mobile TV, it is required that the next generation mobile communication system using E3G/B3G/4G or the like and the next generation wireless system using WiFi or WiMAX or the like support orthogonal frequency division multiplexing (OFDM) and multi-input and multi-output (MIMO) techniques. In the MIMO technique, a plurality of antennas, i.e. an antenna array, can be used for communication transmission on both transmitter side and receiver side. If channels among respective transmitting/receiving antennas are independent of one another, a plurality of parallel spatial channels can be created using the spatial coherence or non-coherence of the antenna array. By transmitting data signals via these parallel spatial channels, signal-to-noise (SNR) will be enhanced significantly and data transmission rates will be increased.

However, in order to enable an antenna array with the MIMO technique on a multimode communication terminal, it is required that the communication terminal comprise more antennas, RF processing modules as well as A/D and D/A converters than those in the configuration depicted in FIG. 1A. This will give rise to the problem of cost and handset structure.

FIG. 1B depicts an exemplary configuration of a multimode communication terminal enabling an antenna array with the MIMO technique in the prior art. A communication terminal 100B comprises three wireless interfaces, namely Bluetooth interface 1100 dedicated to data communication based on the Bluetooth wireless technique, WLAN interface 1200 dedicated to data communication according to the WLAN protocol, and a mobile communication interface 1300B dedicated to data communication according to the mobile communication protocol. Among them, the mobile communication interface 1300B which uses the MIMO technique has an antenna array consisting of antennas 1350-1, 1350-2 and 1350-3, and in correspondence to respective antennas, mobile communication clocks 1320-1, 1320-2 and 1320-3, A/D and D/A converters 1330-1, 1330-2 and 1330-3 as well as mobile communication RF processing modules 1340-1, 1340-2 and 1340-3, to support three mobile communication parallel spatial channels. In mobile communication baseband processor 1310 are correspondingly added functional modules to process spatial signals, such as a spatial filter 1311 and a spatial signal analyzing module 1312 as depicted in FIG. 1B. In an operating state, the three parallel spatial channels formed by the antennas, the RF processing modules as well as the A/D and D/A converters receive/send data signals independently and synchronously (controlled by respective mobile communication clocks). The antennas, the mobile communication RF modules and the A/D and D/A converters respectively belonging to the three parallel spatial channels usually have consistent physical configuration and the same operation characteristics, such as RF central frequency, bandwidth, IF central frequency, baseband sample rate, etc.

Regarding to a wireless mobile communication terminal, good portability is usually necessary, i.e. the spatial size must be as small as possible. Additionally, both the manufacture cost and power supply belong to highly sensitive and key factors during design. On the existing wireless mobile communication terminal, only one RF channel with antenna will occupy ¼ to ⅓ of board area and will cost ⅕ to ¼ engineering bill of material (EBOM). Apparently, to manufacture a wireless mobile communication terminal according to the existing technical solution as depicted in FIG. 1B, the product spatial size will be necessarily increased so as to accommodate added RF channels of a corresponding antenna array. This will cause the increase of manufacture cost and the problem of conspicuous system power supply, which means such kind of multimode communication terminals can hardly meet the requirement in implementation and application and thus cannot occupy the wireless mobile communication terminal market with increasingly fierce competition.

To resolve this problem, a feasible method is to seek RF channel modules (including antennas, RF processing modules, clocks, A/D and D/A converters, etc.) with smaller size and higher integrity in order to reduce the board area of a single RF channel. However, the design of the existing RF channel modules is basically a well-developed technique and leaves little room for improvement. Moreover, even if the board area of a single RF channel is reduced by enhancing system integrity, the reduced margin is inadequate in relation to the expansion of spatial size caused by the several-fold increase of the number of RF channels.

Therefore, there is a need for a novel multimode communication terminal system architecture which enables the MIMO operation mode.

To resolve the problems in the prior art, the present invention provides a switch-based multimode communication terminal system architecture which enables the MIMO operation mode.

SUMMARY

According to a first aspect of the present invention, provided is a computer program product for enabling a MIMO operation mode in a multimode communication terminal, the computer program product includes a tangible storage medium readable by a processing circuit and storing instructions for execution by the processing circuit for performing a method. The method includes switching a first channel module to have parameter characteristics consistent with those of a second channel module, so that the multimode communication terminal enables the MIMO operation mode by using the first channel module and the second channel module at the same time. The method also includes extracting corresponding parameters from the second channel module and configuring the first channel module to be switched with the extracted parameters, such that the first channel module and second channel module enable the multimode communication terminal to perform MIMO communication. The method further includes issuing, upon determination of a switch, notification instructions to means in channel switch layer means and changing a data channel associated with the first channel module, such that the first channel module and second channel module can be adapted to the MIMO operation mode.

According to a second aspect of the present invention, provided is a method for enabling a MIMO operation mode in a multimode communication terminal includes switching a first channel module to have parameter characteristics consistent with those of a second channel module, so that the multimode communication terminal enables the MIMO operation mode by using the first channel module and the second channel module at the same time. The method also includes extracting corresponding parameters from the second channel module and configuring the first channel module to be switched with the extracted parameters, such that the first channel module and second channel module enable the multimode communication terminal to perform MIMO communication. The method further includes issuing, upon determination of a switch, notification instructions to means in channel switch layer means and changing a data channel associated with the first channel module, such that the first channel module and second channel module can be adapted to the MIMO operation mode.

According to a second aspect of the present invention, provided is a multimode communication terminal including a first channel module. The multimode communication terminal also includes a second channel module, the multimode communication terminal can be configured to communicate by using the first channel module and/or the second channel module, the first and second channel modules communicating according to different communication protocols respectively. The multimode communication terminal also includes a channel switch layer means for switching the first channel module to have parameter characteristics consistent with those of the second channel module, such that the multimode communication terminal enables a multiple-input-multiple-output (MIMO) operation mode by using the first channel module and the second channel module at the same time, wherein the MIMO operation mode uses multiple antennas both at a transmitter and a receiver. The channel switch layer means includes a channel module switching means for extracting corresponding parameters from the second channel module, and for configuring at least the first channel module to be switched with the extracted parameters, such that the first channel module and the second channel module enable the multimode communication terminal to perform MIMO communication.

By switching among RF channel modules, the present invention implements with a relatively small number of RF communication modules a wireless mobile multimode communication terminal enabling various operation modes including the MIMO operation mode. Compared with the existing solutions, the present invention greatly reduces the size required by the terminal, decreases the energy consumption required during the operation of the terminal and accordingly enhances the utility of the terminal. Moreover, based on the technical solution of the present invention, a novel, switch-based and unified multimode wireless mobile terminal system architecture can be achieved and thereby the configuration of multimode wireless terminals is further optimized.

Other characteristics and advantages of the present invention will become more apparent from the detailed description of embodiments of the present invention, taken in conjunction with the accompanying drawings.

BRIEF DESCRIPTION OF THE SEVERAL VIEWS OF THE DRAWINGS

Referring to the following accompanying drawings, features and advantages of embodiments of the present invention will be explained in detail. If possible, same or similar reference numerals are used in the accompanying drawings and the corresponding description to designate the same or similar parts, wherein.

DETAILED DESCRIPTION

Figure 1A:
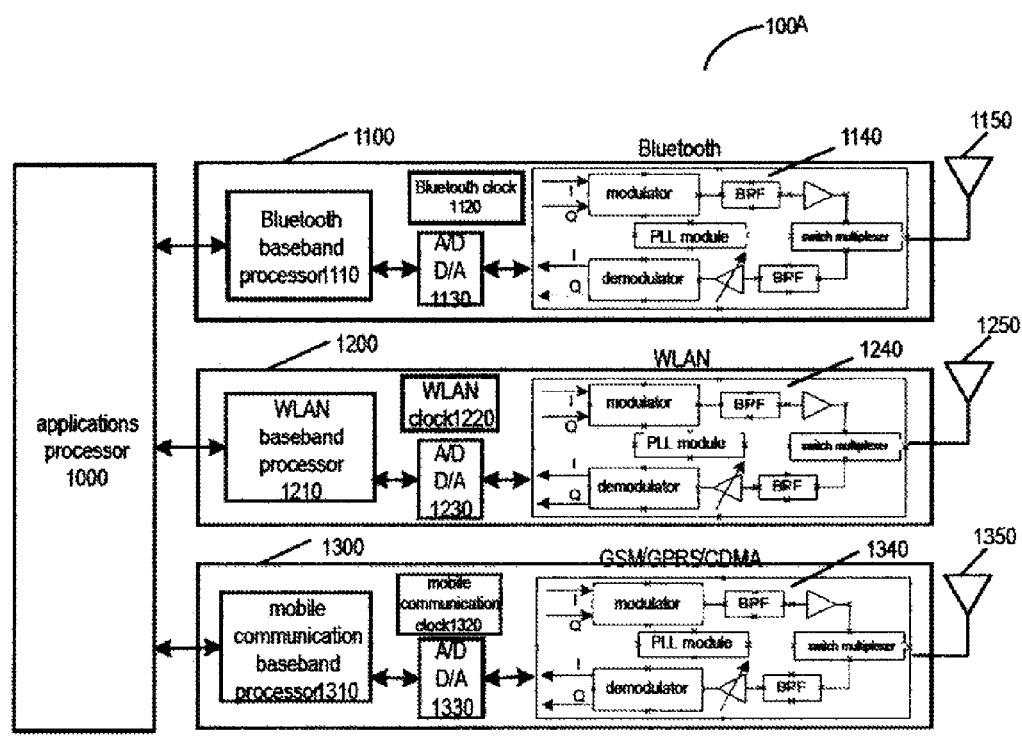
FIG. 1A depicts an exemplary configuration diagram of a multimode communication terminal in the prior art.
Figure 1B:
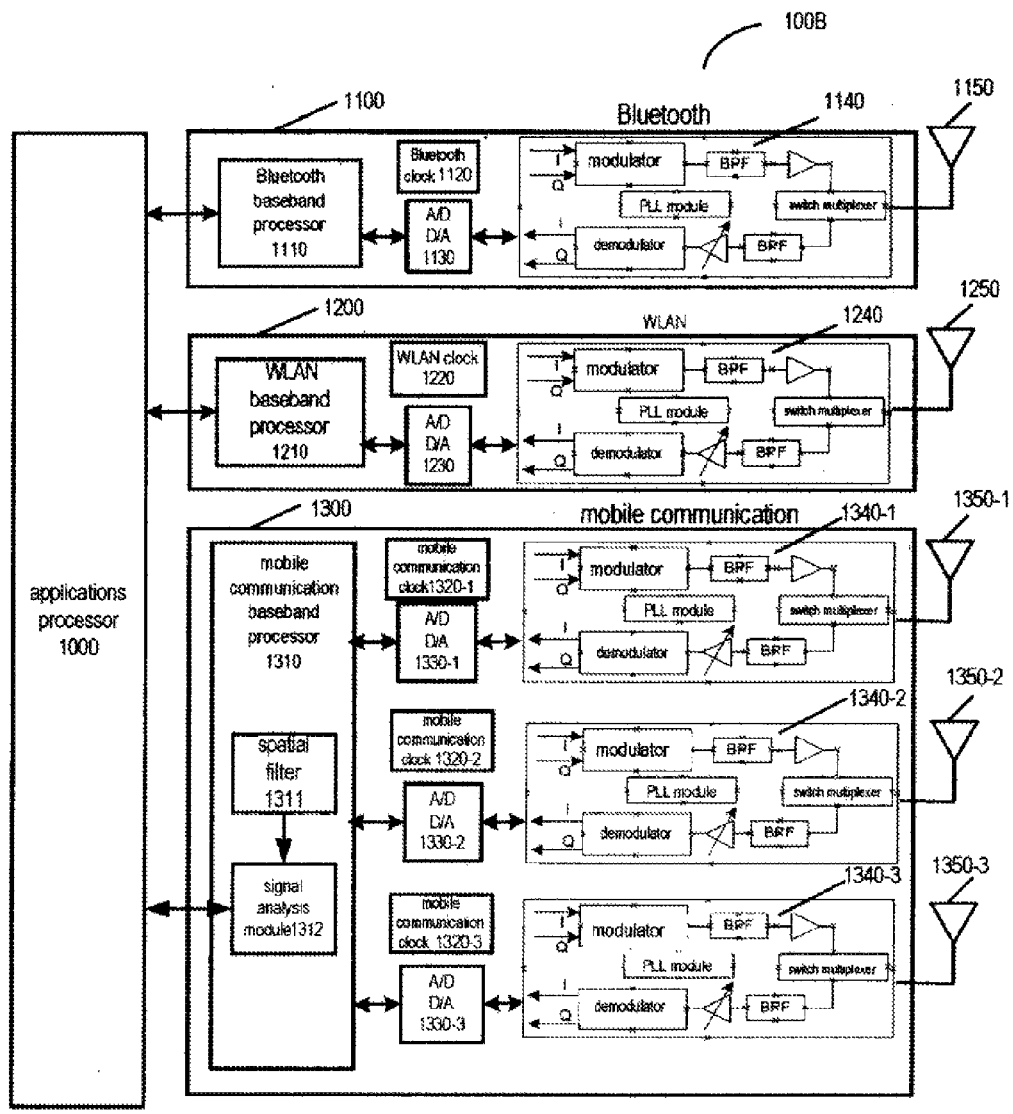
FIG. 1B depicts an exemplary configuration of a multimode communication terminal which enables an antenna array of the MIMO technique in the prior art.

FIGS. 1A and 1B each depict an exemplary configuration of a multimode communication terminal in the prior art. Since they have been set forth in detail in the BACKGROUND, details thereof will not be repeated here.

The technical solution of the present invention is based on such a fact that the current design of multimode communication terminals tends to integrate multiple (e.g. at least two) wireless interfaces into one single smart communication terminal, whereas the actual usage probability of the interfaces significantly decrements with the type number of the interfaces which are used at the same time. Take a multimode communication terminal with three wireless interfaces as an example. In most cases users communicate by using only one type of interface, and in less cases they communicate by using two types of interfaces at the same, and they seldom communicate by using all three types of interfaces at the same time. In other words, even if a multimode communication terminal cannot support users to simultaneously use all wireless interfaces provided by it, the users are unlikely to have a strongly unpleasant experience. That is to say, the users can endure such restrictions against the use of interfaces.

Therefore, the present invention provides a solution of a multimode communication terminal which enables an antenna array, which can support a communication mode using the MIMO technique by utilizing less RF channel modules. The basic idea of the multimode communication terminal according to the present invention is to support an antenna array based on switching in operations. The present invention provides a channel switch layer at the control aspect for the multimode communication terminal. The operating states of the respective channel modules, data flows and data processing procedures corresponding to respective communication modes are switched and controlled by the channel switch layer so that a subset of N wireless interfaces comprised by the multimode communication terminal can serve as a wireless interface of a communication mode supporting the MIMO technique when there is a need to operate in a communication mode supporting the MIMO technique (i.e. the operation mode using an antenna array), wherein the number n of the wireless interfaces comprised in this subset satisfies $2 \leq n \leq N$.

Hereinafter, the present invention will be described in detail in conjunction with various embodiments. The term "connect" and description associated with "connect" as used in the present invention means to include both physical connection and logical connection. Those skilled in the art may understand that different from "physical connection" which means connection with concrete physical lines, "logical connection" stresses mutual association in logical sense (e.g. controlling and being controlled, data exchange). The physical implementation of such association might resort to other relevant physical modules and/or physical lines and/or program codes etc., which are well known to those skilled in the art.

Figure 2:
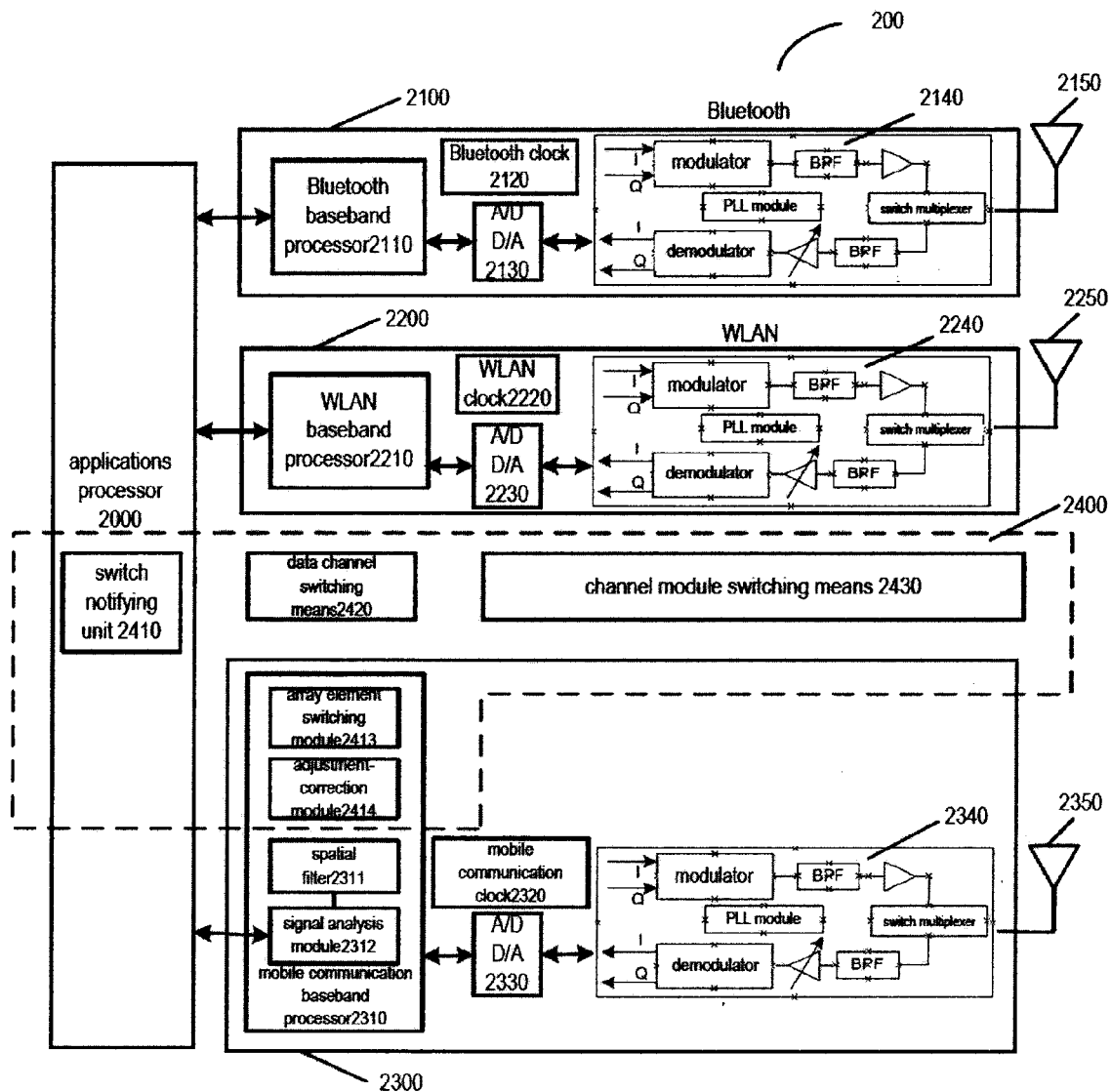
FIG. 2 depicts an exemplary configuration of a multimode communication terminal which enables an antenna array according to an embodiment of the present invention.

FIG. 2 depicts an exemplary configuration of a multimode communication terminal which enables an antenna array according to an embodiment of the present invention.

As depicted in FIG. 2, the configuration of a multimode communication terminal 200 according to an embodiment of the present invention is similar to that of the multimode communication terminal as depicted in FIG. 1A, which comprises: three (N=3) wireless interfaces 2100, 2200 and 2300 as well as an application processor 2000. The multimode communication terminal 200 according to an embodiment of the present invention further comprises a channel switch layer 2400 for switch-controlling respective wireless interfaces (including RF channels and D/A converters) so as to select the current operation states for the respective interfaces according to needs. Normally, the wireless interface 2100 is used for data communication by using a Bluetooth baseband processor 2110, a Bluetooth clock 2120, an A/D and D/A converter 2130, a RF module 2140 as well as an antenna 2150 therein based on the Bluetooth wireless technique; the wireless interface 2200 is used for data communication by using a WLAN baseband processor 2210, a WLAN clock 2220, an A/D and D/A converter 2230, a RF module 2240 as well as an antenna 2250 and according to the WLAN protocol; and wireless interface 2300 is used for data communication by using a mobile communication baseband processor 2310, a mobile communication clock 2320, an A/D and D/A converter 2330, a RF module 2340 as well as an antenna 2350 according to the mobile communication protocol. Under certain conditions (e.g. Quality of Service requirement, user designation, etc.), the mobile communication channel needs to use multiple RF channels so as to adopt a MIMO operation mode. At this point, under the control of the channel switch layer 2400, the operating state of the wireless interface 2100 and/or wireless interface 2200 may be changed to operate as a mobile communication interface. They receive/transmit in the MIMO operation mode mobile communication data together with the wireless interface 2300 according to the mobile communication protocol.

According to this embodiment of the present invention, the channel switch layer 2400 comprises: a switch notifying unit 2410, data channel switching means 2420, channel module switching means 2430, an array element switching module 2413 and optionally, an adjustment-correction module 2414.

The switch notifying unit 2410 may be implemented as a functional module residing on the application processor 2000 or another control processor in the multimode communication terminal 200. When a switch is needed (e.g. required by Quality of Service, designated by a user) and switch conditions are in place, i.e. there is currently at least one idle wireless interface (e.g. the wireless interface 2100 and/or wireless interface 2200), the switch notifying unit 2410 can issue notification instructions to the other modules of the channel switch layer 2400, notifying them to get prepared for switch. The notification instructions may be simple switch instructions indicating an operating state to be switched into or including parameter information related to the switch. As needed, the switch notifying unit 2410 may be configured to select a currently optimum switch policy according to a certain predetermined rule(s), wherein the switch policy may comprise, for example, how to select the number of the wireless interfaces to be switched, how to decide which wireless interface or wireless interfaces can be switched, etc. Such switch policy helps to resolve conflicts which might occur in case that a multimode communication terminal has to be operated simultaneously in more than one modes (for example, since higher communication quality and bandwidth are requested by the current service, the multimode communication terminal 200 has to operate in the communication mode using the MIMO technique, and at that moment, the user issues a request for Bluetooth service via the application interface). However, the design and the implementation of the switch policy are not the problem addressed by the present invention, which are related to such design elements as application scenarios, target performance and target client group and can be adjusted and changed by those skilled in the art.

The channel module switching means 2430 extracts channel parameters of a reference channel (i.e. a wireless interface) according to the switch instructions issued from the switch notifying unit 2410, and configures the wireless interface(s) to be switched with the extracted parameters. Different radio applications, critical characteristics would be different, which may comprise, for example, RF central frequency, IF frequency, bandwidth and baseband sample rate. However, in case of applying these different wireless interfaces to the operation mode using the MIMO technique, respective involved wireless interfaces must have completely the same parameter configuration. In present, expansion of use has been taken into consideration in the design of such modules as antennas, RF modules as well as A/D and D/A converters. That is to say, most of these modules are able to operate in multiple different basebands or relatively broad operation domain value. The channel module switching means 2430 may be connected respectively with the RF modules 2140, 2240 and 2340 and configure the RF module 2140 and/or 2240 with corresponding parameters obtained from the reference RF module 2340. On the other hand, the channel module switching means 2430 is required to provide a D/A conversion clock for the switched wireless interface. In the operation mode using the MIMO technique, since received signals in the respective wireless interfaces have to be D/A and A/D converted at the same baseband sample rate, the switched wireless interface must apply a clock completely synchronous with that of the reference wireless interface. The channel module switching means 2430 will directly provide the clock signal obtained from the mobile communication clock 2320 of the wireless interface 2300 to the A/D and D/A converter 2130 of the wireless interface 2100 to be switched or the A/D and D/A converter 2230 of wireless interface 2200 to be switched, to replace the clock signals provided by Bluetooth clock 2120 and the WLAN clock 2220, respectively.

It should be understood that as the basic functions performed by channel module switching means 2430 have been described above, those skilled in the art may understand that concrete implementation of these functions are associated with reconfiguration manners of respective modules in the wireless interface to be switched. For example, some multimode RF modules are able to convert their operation modes automatically, and thus the channel module switching means 2430 only needs to send a control signal to notify them of switching to a desired operation mode; some RF module may be provided with optional hardware circuit components, and thus the channel module switching means 2430 may be required to deliver detailed parameter values obtained from the reference wireless interface to an designated input of such RF modules so as to convert their operation modes. Therefore, those skilled in the art can design an implementation of the channel module switching means 2430 according to the present invention in light of the hardware configuration of a specific wireless interface, and various implementations are deemed as the modifications of the RF channel module switching means according to the present invention.

The data channel switching means 2420 is used for switching baseband data received from and/or transmitted to the A/D and D/A converter in a switched wireless interface, so that the A/D and D/A converter of the switched wireless interface, in the operation mode using the MIMO technique, exchanges the baseband data with the mobile communication baseband processor 2310 at wireless interface 2300. The mobile communication baseband processor 2310 contains modules adapted to process spatial multiplexing signals in the operation mode using the MIMO technique, such as a spatial filter 2311, a spatial signal analyzer 2312 etc.

It should be understood that as the basic functions performed by the data channel switching means 2420 have been described above, those skilled in the art may understand that concrete implementation of these functions depend on specific circuitry arrangements of the multimode communication terminal. According to an exemplary implementation, the data channel switching means 2420 may comprise such physical components as a switch array and corresponding wirings between the switch array and the mobile communication baseband processor 2310 and between the switch array and the A/D and D/A converters of the respective wireless interfaces to be switched. Therefore, those skilled in the art can design an implementation of the data channel switching means 2420 according to the present invention in light of the specific circuitry arrangement of the multimode communication terminal. Furthermore, various implementations are deemed as modifications of the data channel switching means according to the present invention.

The array element switching module 2413 is used to set an algorithm in accordance with the number n of available array elements in the antenna array, so that the baseband processing of the MIMO signal can be adapted to the current situation of the radio application. Specifically, if the switch notifying unit 2410 notifies the array element switching module 2413 to operate in the operation mode using the MIMO technique in which the number of the array elements in the antenna array is 3 (i.e. both the wireless interfaces 2100 and 2200 are switched to the operation mode using the MIMO technique, for mobile communication together with the wireless interface 2300), then the switch notifying unit 2410 controls to select a algorithm for spatial filtering and signal analysis where the number of antennas is 3. If the switch notifying unit 2410 notifies the array element switching module 2413 to operate in the operation mode using the MIMO technique in which the number of array elements in the antenna array is 2 (i.e. one of the wireless interfaces 2100 and 2200 is switched to the operation mode using the MIMO technique, for mobile communication together with the wireless interface 2300), then the switch notifying unit 2410 controls to select an algorithm for spatial filtering and signal analysis where the number of antennas is 2.

The array element switching module 2413 is preferably implemented as a function module residing on the mobile communication baseband processor 2310. Of course, those skilled in the art can implement array element switching module 2413 as a function module residing on other control processors in the terminal.

Moreover, it should be understood that in some examples, for instance in an example in which the multimode communication terminal is set to be only switched to a MIMO mode using a fixed number of antenna array elements (e.g. 2 or 3), the array element switching module 2413 is not needed. Although this example without the array element switching unit is not preferable because it reduces the flexibility of multimode selection performed by the multimode communication terminal, it can be an alternative embodiment of the present invention.

Alternatively, according to the embodiment of the present invention as depicted in FIG. 2, the channel switching layer 2400 may further comprise an adjustment-correction module 2414, which is mainly used for correcting the difference between respective RF channels that operate in the operation mode using MIMO technique. The basic function and principle of adjustment-correction module 2414 are the same as those of the correction mechanism of a receiver having an antenna array. Since the respective RF channels according to the present invention tend to be much more different in terms of construction and process than the RF channels of the wireless interface 1300B, which are dedicated to enable an antenna array in FIG. 1B, it is preferred that they are corrected and adjusted by the adjustment-correction module 2414, so that the switched MIMO system can operate normally and efficiently. The operating principle of the adjustment-correction module 2414 can be briefed as follows: a target signal spatial feature matrix in which deviation has been cancelled by using the correction procedure can be obtained by multiplying stored correction matrix $\vec{B}$ with the spatial feature matrix of a signal received by the antenna array, which contains the deviation. Before the multimode communication terminal 200 is dispatched from the factory, the manufacturer can test the terminal by using a test signal with known utilization power and an arriving direction, and then the correction matrix $\vec{B}$ is a ratio of the ideal test signal spatial feature matrix $\vec{A}$ to the actual received signal spatial feature matrix $\vec{A}'$, i.e. $\vec{B}=\vec{A}\cdot\vec{A}'^{-1}$. In addition, physical characteristics of each channel thereof might change as the user uses the multimode communication terminal and time goes by, and the correction matrix $\vec{B}$ will changes accordingly. The adjustment-correction module 2414 may be preferably designed to update the correction matrix $\vec{B}$ regularly. For example, the multimode communication terminal regularly requests such network equipment as a base station to send a test signal, and then the adjustment-correction module 2414 automatically tests and updates the correction matrix $\vec{B}$ by using the test signal.

The adjustment-correction module 2414 may be preferably implemented as a function module residing on the mobile communication baseband processor 2310. Of course, those skilled in the art can further implement the adjustment-correction module 2414 as a function module residing on other control processors in the terminal.

Figure 3:
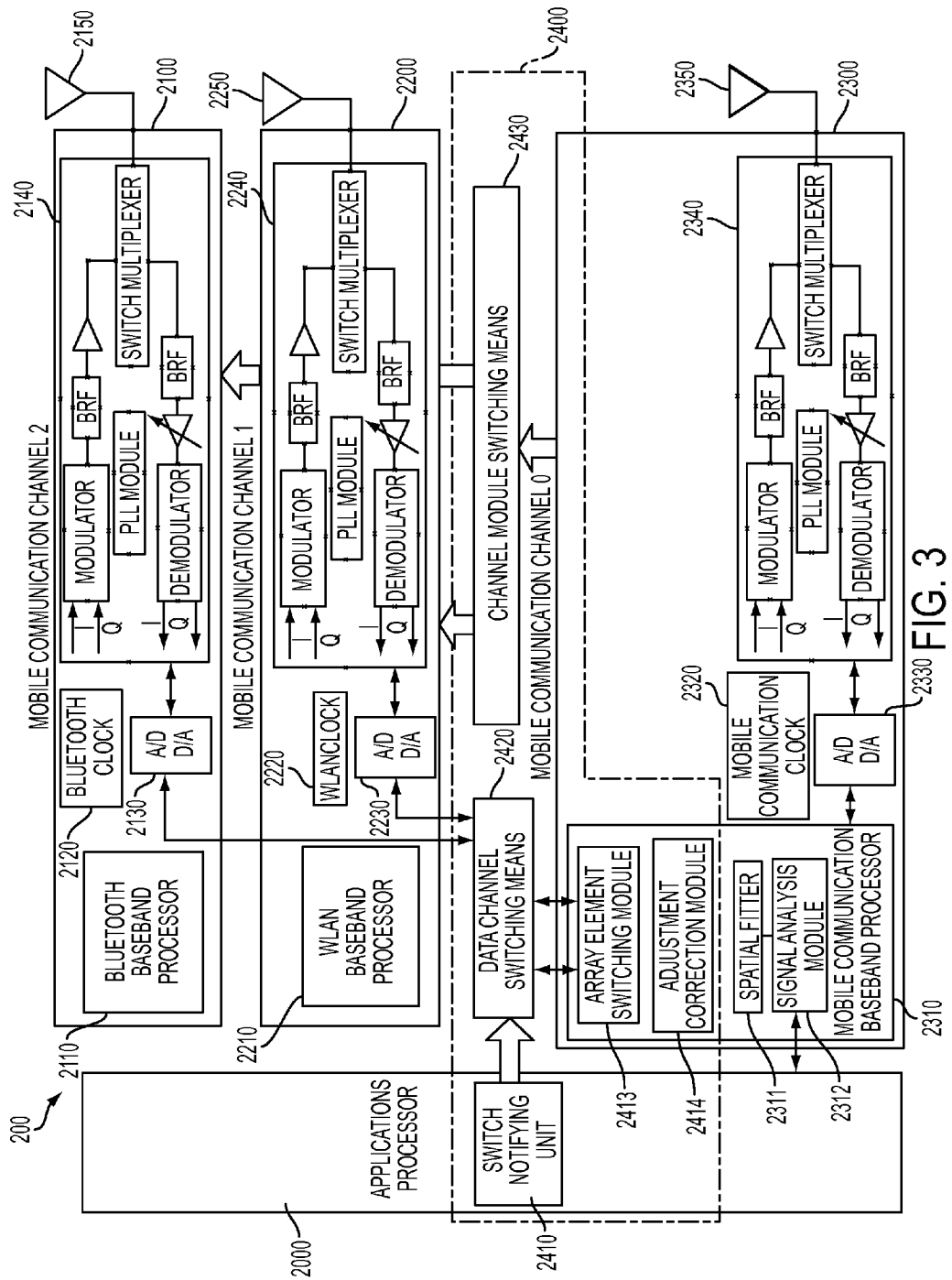
FIG. 3 schematically depicts an operating state in which the multimode communication terminal as depicted in FIG. 2 operates in a communication mode using the MIMO technique.

FIG. 3 schematically depicts an operating state in which the multimode communication mode as depicted in FIG. 2 operates in a communication mode using the MIMO technique.

As depicted in FIG. 3, the switch notifying unit 2410 issues switch instructions to all modules n the channel switch layer 2400, notifying the wireless interfaces 2100 and 2200 to switch into the operation mode using the MIMO technique. According to the instructions, the respective modules can perform their own switch procedures in parallel. The channel module switching means 2430 obtains all required parameters from the reference channel—a mobile communication channel 0 (the wireless interface 2300) and provides them to the wireless interfaces 2100 and 2200, so that the antennas 2150, 2250 and the RF modules 2140, 2240 can operate in the mobile communication operation frequency band and provide the A/D and D/A converters 2130 and 2230 with the clock signal of the mobile communication clock 2320 as their baseband sample clocks. Through the switch procedure, the data channel switching means 2420 causes the A/D and D/A converter 2130 in the wireless interface 2100 and the A/D and D/A converter 2230 in the wireless interface 2200 to exchange data with the mobile communication baseband processor 2310 in the wireless interface 2300 other than with the baseband processors 2110, 2210 in their own wireless interfaces. In this way, the wireless interface 2100 and the wireless interface 2200 work as a mobile communication channel 2 and a mobile communication channel 1 respectively for mobile communication in the MIMO mode together with the wireless interface 2300 (i.e. the wireless mobile communication channel 0). Upon receipt of the switch notification from the switch notifying unit 2410, the array element switching module 2413 switches algorithm required in processing the MIMO signal, for example, a corresponding algorithm used in the spatial filter 2311 and signal analyzing module 2312 to an algorithm adapted to the situation in which the number of array elements in the antenna array is 3. In the downlink direction, signals from the mobile communication channels 0, 1 and 2 are inputted into the mobile communication baseband processor 2310, adjusted by the adjustment-correction module 2414 and then inputted into the spatial filter 2311 and subsequently into the signal analyzing module 2312 in which the received multi-channel spatial multiplexing signals are baseband processed. Next, the resulted data is transferred to the application processor 2000 for subsequent application such as multimedia presentation. In the uplink direction, mobile communication data to be transmitted is transferred to the mobile communication baseband processor 2310 by the application processor 2000 to form baseband signals, which are in turn sent on the mobile communication channels 0, 1 and 2 in the MIMO mode and via the antenna array.

Figure 4:
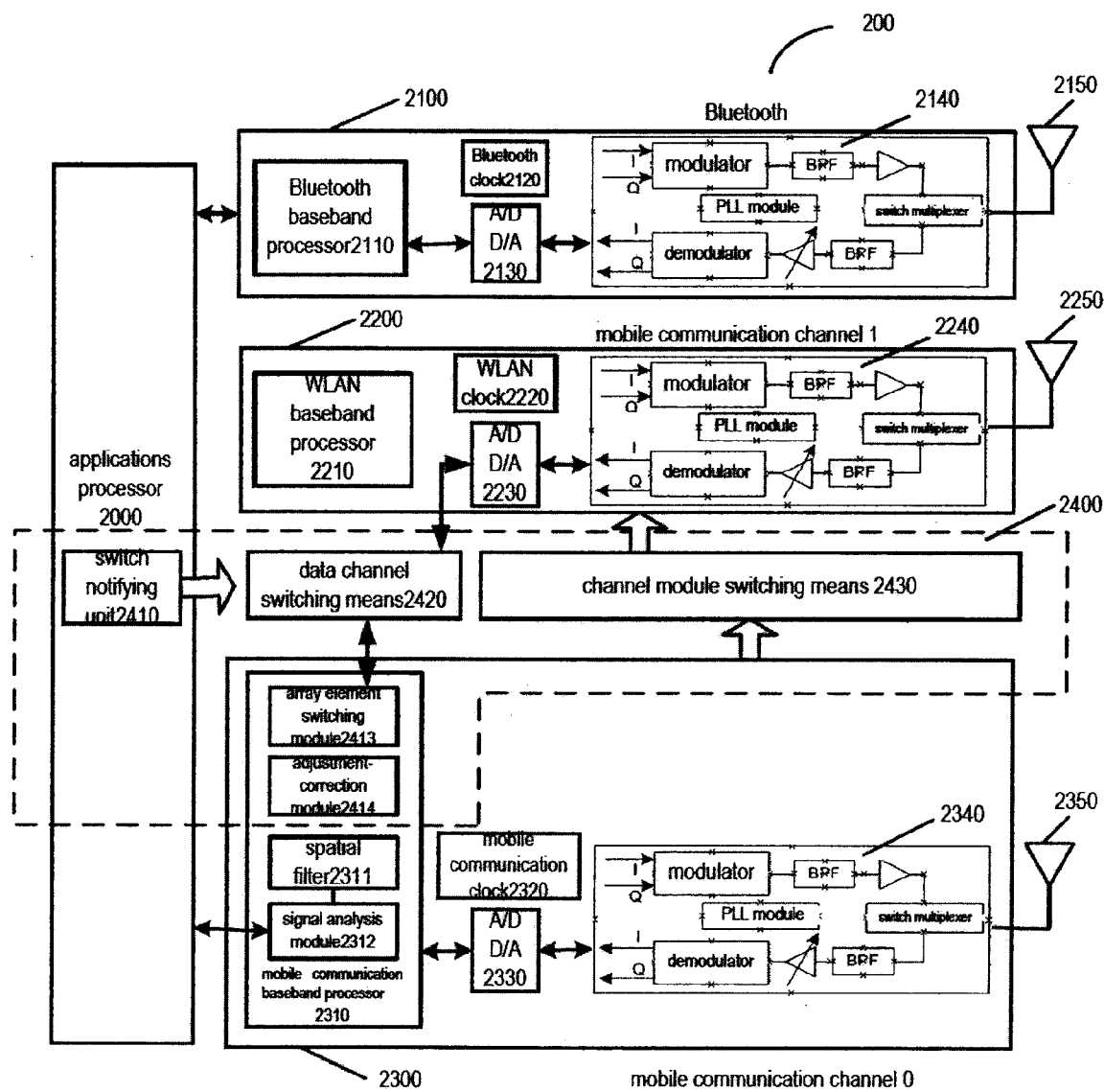
FIG. 4 schematically depicts an operating state in which the multimode communication terminal as depicted in FIG. 2 simultaneously operates in a communication mode using the MIMO technique and in another mode.

FIG. 4 schematically depicts an operating state in which the multimode communication terminal as depicted in FIG. 2 simultaneously operates in both a communication mode using the MIMO technique and another mode.

As depicted in FIG. 4, the switch notifying unit 2410 issues switch instructions to all modules in the channel switch layer

2400, notifying the wireless interface 2200 to switch into the operation mode using the MIMO technique, while the wireless interface 2100 keeps the existing communication based on the Bluetooth technique. According to the instructions, the respective modules can perform their own switch procedures in parallel. The channel module switching means 2430 obtains all required parameters from the reference channel—the mobile communication channel 0 (the wireless interface 2300) and provides them to the wireless interface 2200, so that the antenna 2250 and the RF module 2240 can operate in the mobile communication operation frequency band and provide the A/D and D/A converter 2230 with the clock signal of the mobile communication clock 2320 as its baseband sample clocks. Through the switch procedure, the data channel switching means 2420 causes the A/D and D/A converter 2230 in the wireless interface 2200 to exchange data with the mobile communication baseband processor 2310 in the wireless interface 2300 other than with the WLAN baseband processor 2110 in the wireless interface 2200. At the same time, the data channel switching means 2420 keeps data exchange between the A/D and D/A converter 2130 and the Bluetooth baseband processor 2110 in the wireless interface 2100. In this way, the wireless interface 2200 work as a mobile communication channel 1 for mobile communication in the MIMO mode together with the wireless interface 2300 (i.e. the wireless mobile communication channel 0), and the wireless interface 2100 works as the Bluetooth interface for data communication based on the Bluetooth wireless technique. Upon receipt of the switch notification from the switch notifying unit 2410, the array element switching module 2413 switches algorithm required in processing the MIMO signal, for example, a corresponding algorithm used in the spatial filter 2311 and the signal analyzing module 2312 to an algorithm adapted to the situation in which the number of array elements in the antenna array is 2. In the downlink direction, signals from the mobile communication channels 0 and 1 are inputted into the mobile communication baseband processor 2310, adjusted by the adjustment-correction module 2414 and then inputted into the spatial filter 2311 and subsequently into the signal analyzing module 2312 in which the received multi-channel spatial multiplexing signals are baseband processed. Next, the resulted data is transferred to the application processor 2000 for subsequent application such as multimedia presentation. Signals from the Bluetooth communication channel are processed by the Bluetooth baseband processor 2110 and then inputed into the application processor 2000 for subsequent processing. In the uplink direction, mobile communication data to be transmitted is transferred to the mobile communication baseband processor 2310 by the application processor 2000 to form baseband signals, which are in turn sent on then mobile communication channels 0 and 1 in the MIMO mode and via the antenna array; and Bluetooth data to be transmitted is transferred to the Bluetooth baseband processor 2210 by the application processor 2000 to form Bluetooth baseband signals, which are in turn transmitted in the Bluetooth channel.

The embodiment as depicted in FIG. 2 has been described in detail, and its two typical operating states haven been described with reference to FIGS. 3 and 4. The embodiment as depicted in FIG. 2 provides a solution for a multimode communication terminal enabling an antenna array based on the architecture of the current multimode communication terminal. Such a solution can support the MIMO communication mode through the switch procedure merely by adding the channel switch layer to the existing terminal without adding or changing the existing wireless interfaces. The advantage of this solution is that the manufacturer can directly modify the existing terminal to obtain the expansion function of the new MIMO mode, thereby saving the design and manufacture costs.

It is advantageous to use the embodiment depicted in FIG. 2 as a transition solution compatible with the existing products. However, for an ultimate solution, a unified architecture is desired for the multimode communication terminal according to the present invention.

Figure 5:
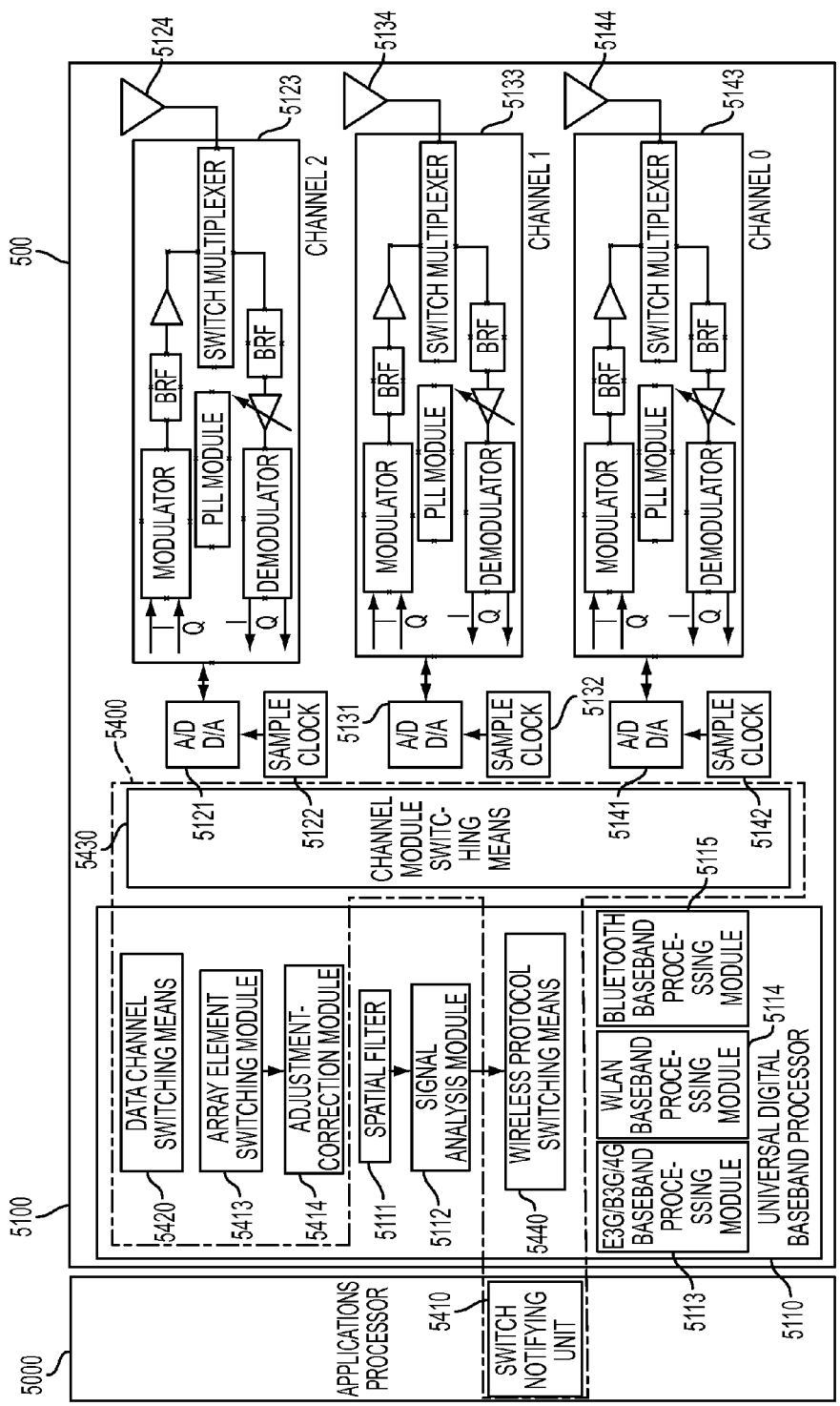
FIG. 5 depicts an exemplary configuration of a multimode communication terminal which enables an antenna array according to another embodiment of the present invention.

FIG. 5 depicts an exemplary configuration of a multimode communication terminal enabling an antenna array according to another embodiment of the present invention. The multimode communication terminal according to this embodiment of the present invention provides a more flexible RF solution for the antenna array mode and other various radio applications. Compared with FIG. 2, a multimode communication terminal 500 as depicted in FIG. 5 has a more unified and optimized configuration.

As depicted in FIG. 5, the multimode communication terminal 500 may support, for example, three communication protocols (i.e. support three communication modes), including the mobile communication protocol E3G/B3G/4G, the WLAN protocol and the Bluetooth protocol. The multimode communication terminal 500 is provided with a unified wireless interface 5100 instead of special interfaces for communicating according to respective protocols, to exchange data with an application processor 5000 and thereby perform data communication according to a corresponding protocol. The unified wireless interface 5100 comprises a universal digital baseband processor 5110 and three sets of channel modules (including antennas, RF processing modules, clocks, A/D and D/A converters etc.).

The digital baseband processor 5110 incorporates the baseband processors used for these three communication protocols, namely an E3G/B3G/4G baseband processing module 5113, a WLAN baseband processing module 5114 and a Bluetooth baseband processing module 5115. During communication based on the mobile communication protocol E3G/B3G/4G, the terminal, under certain conditions, needs to operate in the MIMO operation mode i.e., receive and send data using an antenna array. Therefore, like the mobile communication baseband processor 2310 as depicted in FIG. 2, the universal digital baseband processor 5110 further comprises a spatial filter 5111 and a signal analyzing module 5112, which are used for processing MIMO spatial multiplexing signals. Moreover, the universal digital baseband processor 5110 is also used for carrying out part of functions of the channel switch layer, which will be set forth in detail below.

Each of the three sets of the channel modules comprises an antenna, a RF processing module, a clock as well as an A/D and D/A converter. Preferably, corresponding components in the respective sets of channel modules may have the same or similar configuration and characteristics. This facilitates unifying the design and manufacture of the channel modules, thereby optimizing the arrangement of the channel modules and reducing its area on the terminal. Moreover, this can shrink the characteristic difference of the respective channels in construction, process and other aspects and helps multimode communication mode 500 to operate in the MIMO mode normally and efficiently.

The multimode communication terminal 500 further comprises a channel switch layer 5400 used for switching the terminal's operating state (mode). In this embodiment, Selection of the operation mode in which the multimode communication terminal 500 operates is totally controlled by the channel switch layer 5400. Through the switch procedure, the channel switch layer 5400 can configure any channel to operate according to any one of the three protocols. The channel switch layer 5400 comprises a switch notifying unit 5410, data channel switching means 5420, channel module switching means 5430, an array element switching module 5413 and an optional adjustment-correction module 5414. The channel switch layer 5400 further comprises a wireless protocol switching means 5440.

Like the switch notifying unit 2410 in the embodiment as depicted in FIG. 2, the switch notifying unit 5410 may be implemented as a functional module residing on application processor 5000 or another control processor in the multimode communication terminal 500. The switch notifying unit 5410 issues instructions to other modules on the channel switch layer 5400, notifying them of a state to be switched into. Likewise, the switch notifying unit 5410 can be configured to select a currently optimum switch policy based on a certain predetermined rule(s) which, for example, may comprise: how to select the number of the wireless interfaces to be switched, how to decide which wireless interface or wireless interfaces can be switched, etc. It should be noted that in this embodiment, the operating state of the multimode communication terminal 500 is determined through switch by the channel switch layer 5400, instead of being limited by the channel modules per se. Therefore, the optimum switch policy which the switch notifying unit 5410 is based on is somewhat different from that in the embodiment as depicted in FIG. 2. However, those skilled in the art can adjust and change the policy to adapt it to the present embodiment without the exercise of inventive skill.

Like the channel module switching means 2430 as depicted in FIG. 2, the channel module switching means 5430 extracts channel parameters of a reference channel (i.e. a wireless interface) according to the switch instructions issued from the switch notifying unit 5410, and configures the wireless interface(s) to be switched with the extracted parameters. In this embodiment, the channel module switching means 5430 may use any channel as the reference channel and extract the desired parameters or obtain a corresponding signal (such as a control signal) therefrom. According to the received switch notification, the channel module switching means 5430 can configure modules of any channel by using the obtained parameters or corresponding signal, in order to perform a switch procedure. It should be understood that a more flexible switch procedure is achieved in this embodiment.

Like the data channel switching means 2420 as depicted in FIG. 2, the data channel switching means 5420 is used for switching baseband data from and/or to the A/D and D/A converter, so as to process corresponding baseband data by using a corresponding baseband processing module. Since a unified wireless interface architecture is adopted in this embodiment, preferably, the data channel switching means 5420 may be implemented as a functional module residing on the universal digital baseband processor 5110. In such way, all A/D and D/A converters may exchange baseband data with the universal digital baseband processor 5110 directly. Then, soft routing of the baseband data is performed by the data channel switching means 5420. For example, when the three channels operate in a mobile communication mode of MIMO state, the data channel switching means 5420 switches baseband signals from the three channels to the signal data processing channel including the spatial filter 5111 and the signal analyzer 5112, which are then connected to the E3G/B3G/4G baseband processing module 5113. The functions of the data channel switching means 5420 will become more apparent from the detailed description of the multimode communication terminal 500.

According to the embodiment as depicted in FIG. 5, the channel switch layer 5400 further comprises a wireless protocol switching means 5440 used for assisting data channel switching means 5420 in selecting a proper baseband processing module for baseband data. It is advantageous to configure the wireless protocol switching means 5440 in the case that the multimode communication terminal 500 operates in a hybrid mode (e.g. operates in a hybrid mode of the mobile communication mode and the Bluetooth mode). The wireless protocol switching means 5440 may be implemented as a functional module residing on the universal digital baseband processor 5110, and the functions thereof will become more apparent from the description of the multimode communication terminal 500.

The function and usage of the array element switching module 5413 and the optional adjustment-correction module 5414 are similar to those of the array element switching module 2413 and the optional adjustment-correction module 2414 as depicted in FIG. 2, and details thereof are omitted.

Those skilled in the art may understand that various modifications can be made to the configuration of the multimode communication terminal 500 as depicted in FIG. 5. For example, since each sample clock is associated with a baseband sample rate of a radio application fixedly, to achieve more flexible channel distribution, each clock signal may be dispatched to a corresponding A/D and D/A converter by channel module switching means 5430, instead of being provided by the sample clock. Of course, such a modification requires the arrangement of the channel module switching means 5430 to change accordingly.

Figure 6:
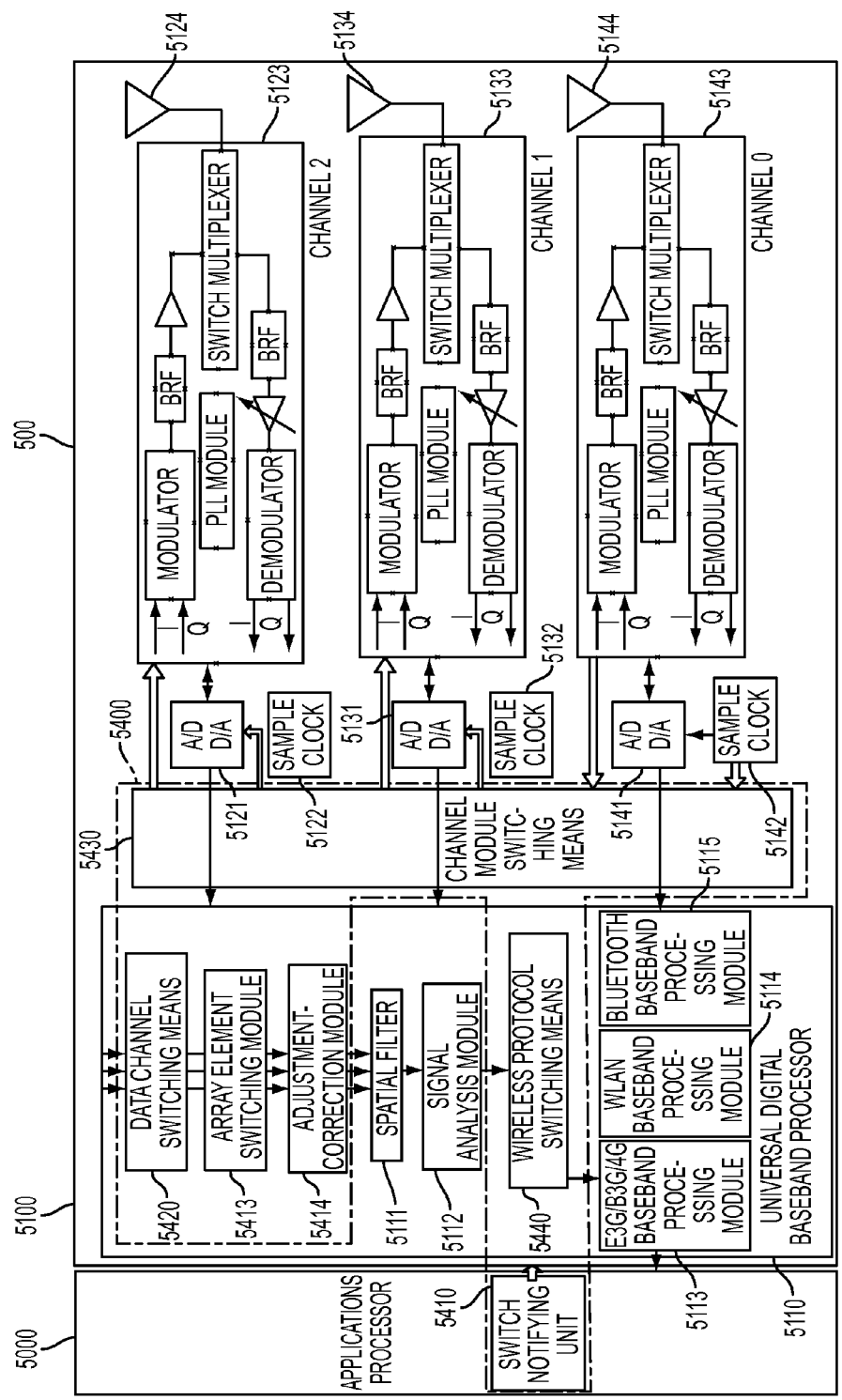
FIG. 6 schematically depicts an operating state in which the multimode communication terminal as depicted in FIG. 5 operates in a communication mode using the MIMO technique.

FIG. 6 schematically depicts an operating state in which the multimode communication terminal as depicted in FIG. 5 operates in a communication mode using the MIMO technique.

As depicted in FIG. 6, the switch notifying unit 5410 issues switch instructions to all modules on the channel switch layer 5400, notifying all channels of switching into the operation mode using the MIMO technique. According to the instructions, the respective modules perform their own switch procedures in parallel. The channel module switching means 5430 obtains all required parameters from a reference channel (any channel can be used as the reference channel, which is assumed to be the mobile communication channel 0 here), configure the channels 1 and 2 using these obtained parameters so that the antennas 5150, 5250 and the RF modules 5140, 5240 operate in the mobile communication operation frequency band, and provides the A/D and D/A converters 5130, 5230 and 5330 with clock signals of mobile communication clock 5320 as their baseband sample clocks. In the downlink direction, the data channel switching means 5420 switches mobile communication MIMO data from the three wireless channels to a signal data processing channel including the adjustment-correction module 5414, the spatial filter 5111 and the signal analyzer 5112. Upon receipt of the switch notification from the switch notifying unit 5410, the array element switching module 5413 switches algorithm required in processing the MIMO signal, for example, a corresponding algorithm used in the spatial filter 5311 and the signal analyzing module 5312 to an algorithm adapted to the situation in which the number n of array elements in the antenna array is 3. According to the switch notification from the switch notifying unit 5410, the wireless protocol switching means 5440 feeds inputted mobile communication data to the corresponding E3G/B3G/4G baseband processing module 5113 which then transfers the processed data to the application processor 5000 for subsequent application. The data flow and data processing in the uplink direction are similar to those in the downlink direction, and description thereof is omitted.

Figure 7:
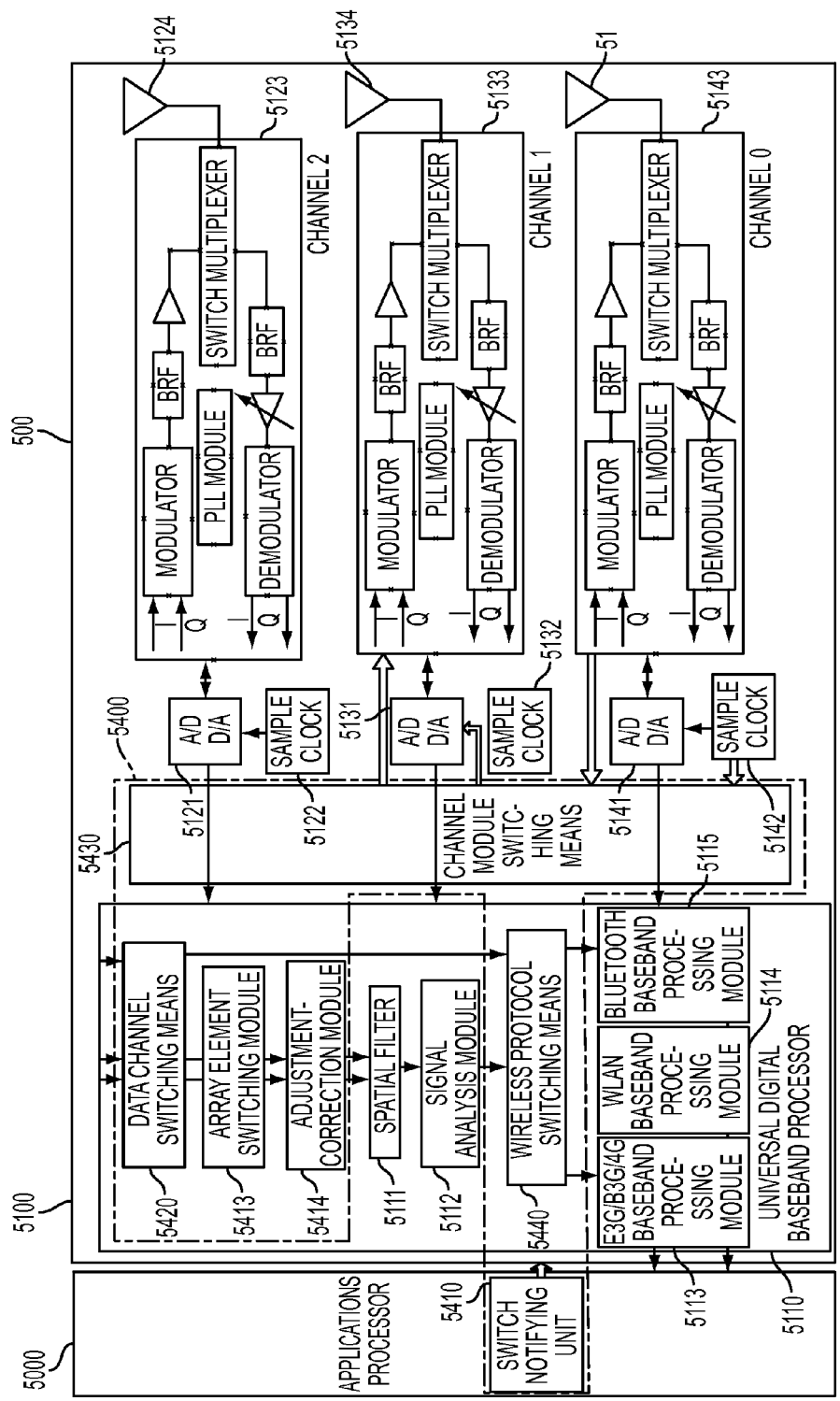
FIG. 7 schematically depicts an operating state in which the multimode communication terminal as depicted in FIG. 5 simultaneously operates in a communication mode using the MIMO technique and in another mode.

FIG. 7 schematically depicts an operating state in which the multimode communication terminal as depicted in FIG. 5 simultaneously operates in a communication mode using the MIMO technique and another mode.

As depicted in FIG. 7, the switch notifying unit 5410 issues switch instructions to all modules on the channel switch layer 5400, notifying the channels 0 and 1 to switch into the operation mode using the MIMO technique, while the channel 2 keeps the original communication based on the Bluetooth technique. According to the instructions, the respective modules perform their own switch procedures in parallel. The channel module switching means 5430 obtains all required parameters from a reference channel (any channel can be used as the reference channel, which is assumed to be the mobile communication channel 0 here), configures channel 1 using the obtained parameters so that the antenna 5250 and the RF module 5240 to operate in the mobile communication operation frequency band, and provides the A/D and D/A converters 5230 and 5330 with clock signals of the mobile communication clock 5320 as their baseband sample clocks; the channel module switching means 5430 causes the antenna 5150 and the RF module 5140 to operate in the Bluetooth protocol operation frequency band and provides the A/D and D/A converter 5130 with a clock signal of Bluetooth clock 5120 as its baseband sample clock. In the downlink direction, the data channel switching means 5420 switches mobile communication MIMO data from the channels 0 and 1 to a signal data processing channel including the adjustment-correction module 5414, the spatial filter 5111 and the signal analyzer 5112; and the data channel switching means 5420 switches Bluetooth baseband signals from the RF channel 2 to the wireless protocol switching means 5440 directly. Upon receipt of the switch notification from the switch notifying unit 5410, the array element switching module 5413 switches algorithm required in processing the MIMO signal, for example, a corresponding algorithm used in the spatial filter 5311 and the signal analyzing module 5312 to an algorithm adapted to the situation in which the number n of array elements in the antenna array is 2. According to the switch notification from the switch notifying unit 5410, the wireless protocol switching means 5440 feeds inputted mobile communication data to the corresponding E3G/B3G4G baseband processing module 5113; the wireless protocol switching means 5440 feeds inputted Bluetooth data to the corresponding Bluetooth baseband processing module 5115. Then, the E3G/B3G/4G baseband processing module 5113 and the Bluetooth baseband processing module 5115 transfer the processed data (both mobile communication data and Bluetooth data) to the application processor 5000 for subsequent application. The data flow and data processing in the uplink direction are similar to those in the downlink direction, and description thereof is omitted.

Figure 8:
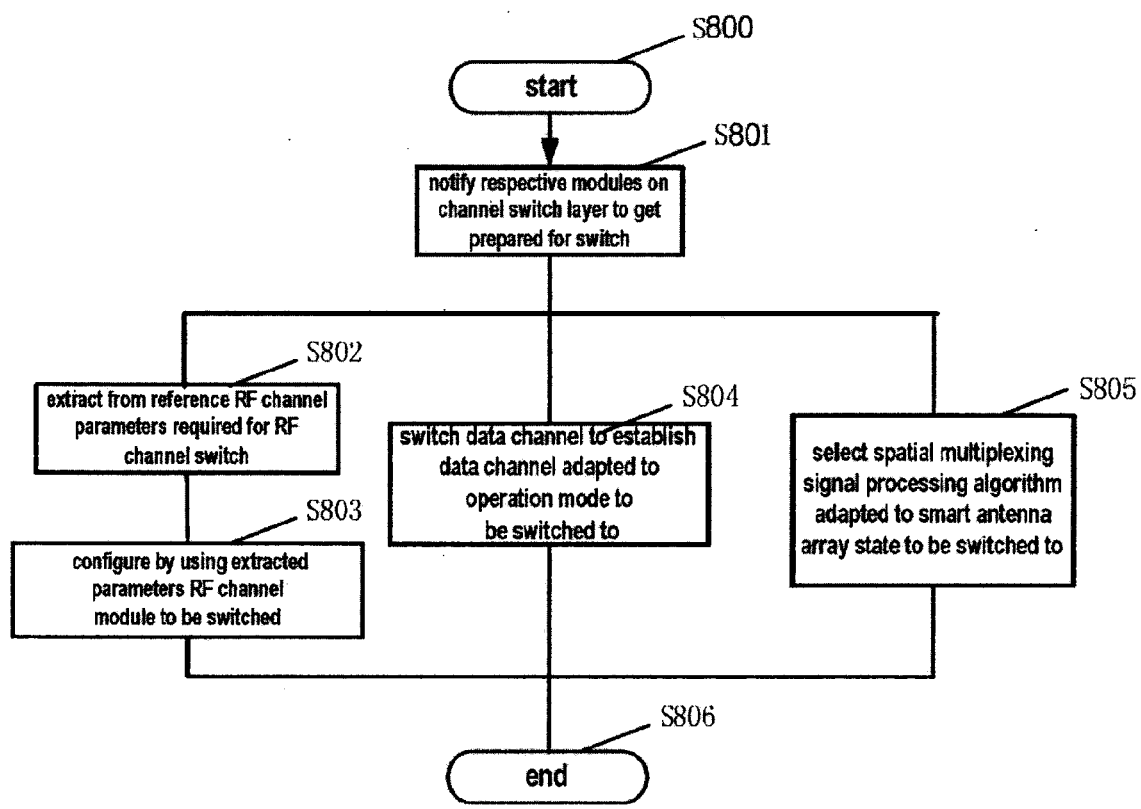
FIG. 8 depicts a flowchart of a method of enabling a MIMO operation mode through switch on a multimode communication terminal according to an embodiment of the present invention.

FIG. 8 depicts a flowchart of a method of enabling a MIMO operation mode through switch on a multimode communication terminal according to a preferred embodiment of the present invention.

In step S800, the multimode communication terminal according to the present invention begins a switch procedure. The switch procedure is started when a switch is necessary (e.g. required by Quality of Service, designated by a user) and the current wireless interfaces meet some switch conditions. According to the previous description, whether or not the switch procedure is started is associated with the switch policy implemented in the multimode communication terminal Any modification and variation can be made by those skilled in the art.

In step S801, each switch module on the channel switch layer of the multimode communication terminal according to the present invention is notified to get prepared for switch. Depending on the specific implementation of the multimode communication terminal, this notification may be a simple switch signal or instructions indicating an operating state to be switched into, or a complex command containing other parameter information associated with the switch. Here, suppose this notification indicates each switch module to switch from a non-MIMO operation mode (e.g. the wireless interfaces (RF channels) operate respectively in the Bluetooth mode, WLAN mode and mobile communication mode) to a MIMO operation mode using an antenna array (e.g. the states as depicted in FIGS. 3, 4 or FIGS. 6, 7).

In one aspect, a switch of channel modules is preformed in the switch procedure. In step S802, parameters required for switching a channel are extracted from a reference channel. Depending on the concrete switch mechanism adopted by the channel components in the multimode communication terminal, these parameters may be concrete parameters of RF characters adapted by the radio application to be switched into, including RF central frequency, IF frequency, bandwidth, baseband sample rate etc., or may be only simple switch signals (containing instructions). In particular, a sample clock of the reference channel needs to be extracted in order to ensure that respective MIMO channels can operate with a completely synchronous clock after the switch procedure.

In step S803, the channel module to be switched is configured with the obtained parameters. Depending on the hardware configuration of specific channel modules, the procedure of configuring the channel module with the parameters might be different in this step. For example, a control signal can be sent to the RF module to indicate it to switch into a desired operation mode; or specific parameter values can be delivered to a designated input of the RF module to convert its operation mode. In particular, the sample clock extracted from the reference channel needs to be provided to the channel to be switched in order to ensure that respective MIMO channels can operate with a completely synchronous clock after the switch procedure.

A switch of data channels is then performed in this switch procedure. In step S804, data channels are switched in order to set up a data channel adapted to the operation mode to be switched into. For example, in the present example, that is, during switching from a non-MIMO operation mode (e.g. the wireless interfaces operate respectively in the Bluetooth mode, WLAN mode and mobile communication mode) to a MIMO operation mode using an antenna array (e.g. states as depicted in FIGS. 3, 4 or FIGS. 6, 7), a data channel has to be established between the channels to be switched into the MIMO operation mode and the respective modules for processing spatial multiplexing signals of the MIMO operation mode.

A switch of corresponding algorithms may further performed in the switch procedure. In step S805, which is optional, an algorithm for processing a spatial multiplexing signal is selected, which is adapted to the antenna array state to be switched into. For example, during switching from a non-MIMO operation mode to the MIMO operation mode using an antenna array as depicted in FIG. 3 or 6, an algorithm for processing spatial multiplexing signal is selected, which is adapted to the situation in which the number of antenna array elements is 3; during switching from a non-MIMO operation mode to the MIMO operation mode using an antenna array as depicted in FIG. 4 or 7, an algorithm for processing spatial multiplexing signal is selected, which is adapted to the situation in which the number of antenna array elements is 2. It should be understood that in some examples, the optional step S805 of another aspect of the switch procedure can be omitted (this step is not needed in an exemplary case that the multimode communication terminal is configured to be only switched into a MIMO mode using a fixed number of antenna array elements). Although this example without step S805 is not preferable because it reduces the flexibility of multimode selection preformed by the multimode communication terminal, it can be an alternative embodiment of the present invention.

The procedure is ended in step S806.

Figure 9:
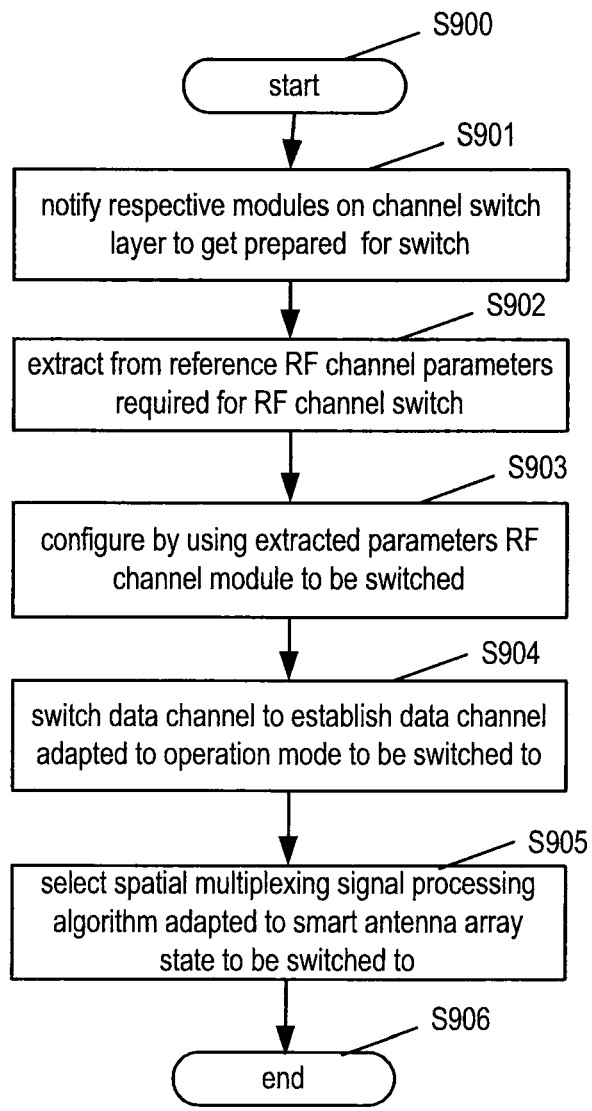
FIG. 9 depicts a flowchart of a method of enabling a MIMO operation mode through switch on a multimode communication terminal according to an embodiment of the present invention.

In the example as depicted in FIG. 8, the respective aspects of this switch procedure are performed in parallel. The respective aspects of the switch are performed in series as depicted in FIG. 9 (description of the respective steps as depicted in FIG. 9 is similar to that as depicted in FIG. 8 and thus is omitted here) or in a combination of series and parallel (not depicted). This relies on the specific circuitry design adopted in the multimode communication terminal and accordingly the matching among various signals during the switch procedure. Therefore, it can be understood by those skilled in the art that any switch procedure performed in any order can be used as a specific implementation of the present invention, provided it will achieve the object of the present invention.

According to other embodiments of the present invention, the method of enabling a MIMO operation mode through switch in a multimode communication terminal can comprise other additional step(s). In an embodiment, the step of switching data channels (in step S804) further comprises the step of selecting a baseband processing module to obtain baseband data from it or provide it with baseband data.

The flowchart of FIG. 8 and the corresponding explanation thereof set forth a typical switch procedure in which the multimode communication terminal according to the present invention switches from a non-MIMO operation mode to a MIMO operation mode. However, it should be understood that the switch procedure in which the multimode communication terminal according to the present invention switches from a non-MIMO operation mode to a MIMO operation mode is similar to a reverse switch procedure with respect to the procedure depicted in FIG. 8. The switch procedure of switching from a non-MIMO operation mode to another non-MIMO operation mode can be implemented as a switch procedure similar to that well known in the present field. In addition, the switch procedure of switching from a MIMO operation mode to another MIMO operation mode (if necessary) is similar to the flow as depicted in FIG. 8 and can be implemented by adaptively adjusting the specific implementation of the respective steps.

Although the embodiments of the present invention have been described with reference to the accompanying drawings, those skilled in the art can make various modifications or alterations within the scope defined by the claims as appended.

What is claimed is:

1. A computer program product for enabling a MIMO operation mode in a multimode communication terminal, the computer program product comprising:
   a non-transitory tangible storage medium readable by a processing circuit and storing instructions for execution by the processing circuit for performing a method comprising:
   switching a first channel module to have parameter characteristics consistent with those of a second channel module, so that said multimode communication terminal enables said MIMO operation mode by using said first channel module and said second channel module at the same time;
   extracting corresponding parameters from said second channel module;
   configuring said first channel module to be switched with said extracted parameters, such that said first channel module and said second channel module enable said multimode communication terminal to perform MIMO communication;
   issuing, upon determination of a switch, notification instructions to means in channel switch layer means; and
   changing a data channel associated with said first channel module, such that said first channel module and said second channel module can be adapted to said MIMO operation mode;
   wherein said step of changing said data channel is performed according to the notification instruction of said switch notifying unit;
   wherein said step of extracting and configuring parameters is performed according to the notification instructions of said switch notifying unit; and
   wherein said parameters from said second channel module include specific operating state parameters of channel modules and/or signals controlling operating states of the channel modules.

2. The computer program product according to claim 1, wherein:
   said step of extracting corresponding parameters further comprises a step of extracting a reference sample clock signal from said second channel module;
   said step of configuring said first channel module further comprises a step of providing said first channel module to be switched with said reference sample clock signal as a sample clock thereof.

3. The computer program product according to claim 2, wherein said switching step further comprises the step of:
   selecting a spatial multiplexing signal processing algorithm which is adapted to an antenna array state of said MIMO operation mode to be switched to;
   wherein the step of selecting is performed according to the notification instructions of said switch notifying unit.

4. The computer program product according to claim 2, wherein said switching step further comprises the step of:
   correcting a channel difference of said channel modules which are switched to said MIMO operation mode;
   wherein the step of correcting said channel difference is performed according to the notification instructions of said switch notifying unit.

5. The computer program product according to claim 2, wherein said switching step further comprises the step of:
   arranging said switch of said channel modules in a unified way, such that said multimode communication mode can freely operate in desired operation mode by using one or more of said channel modules.

6. The computer program product according to claim 5, wherein said step of changing said data channel associated with the channel module further comprises the step of:
   arranging said data channels associated with said channel modules in a unified way, such that said channel modules can be adapted to a desired operation mode;
   wherein said step of arranging data channels in a unified way comprises a step of establishing data channels from the respective channel modules to the proper baseband processing modules according to a current operation mode of said multimode communication terminal.

7. The computer program product according to claim 1, wherein said channel module comprises:
- an antenna;
- a RF processing module;
- a sample clock; and
- an A/D and D/A converter.

8. The computer program product according to claim 1, wherein said different communication protocols of said first and second channel modules are selected from the group consisting of: a Bluetooth communication protocol, a WLAN communication protocol and a mobile communication protocol.

9. A method for enabling a MIMO operation mode in a multimode communication terminal, the method comprising: switching a first channel module to have parameter characteristics consistent with those of a second channel module, so that said multimode communication terminal enables said MIMO operation mode by using said first channel module and said second channel module at the same time; extracting corresponding parameters from said second channel module, wherein said parameters from said second channel module include specific operating state parameters of channel modules and/or signals controlling operating states of the channel modules; configuring said first channel module to be switched with said extracted parameters, such that said first channel module and said second channel module enable said multimode communication terminal to perform MIMO communication; issuing, upon determination of a switch, notification instructions to means in channel switch layer means; and changing a data channel associated with said first channel module, such that said first channel module and said second channel module can be adapted to said MIMO operation mode.

10. The method according to claim 9, wherein said switching step further comprises the step of:
- selecting a spatial multiplexing signal processing algorithm which is adapted to an antenna array state of said MIMO operation mode to be switched to;
- wherein the step of selecting is performed according to the notification instructions of said switch notifying unit.

11. The method according to claim 9, wherein said switching step further comprises the step of:
- correcting a channel difference of said channel modules which are switched to said MIMO operation mode;
- wherein the step of correcting said channel difference is performed according to the notification instructions of said switch notifying unit.

12. The method according to claim 9, wherein said switching step further comprises the step of:
- arranging said switch of said channel modules in a unified way, such that said multimode communication mode can freely operate in desired operation mode by using one or more of said channel modules.

13. The method according to claim 12, wherein said step of changing said data channel associated with the channel module further comprises the step of:
- arranging said data channels associated with said channel modules in a unified way, such that said channel modules can be adapted to a desired operation mode;
- wherein said step of arranging data channels in a unified way comprises a step of establishing data channels from the respective channel modules to the proper baseband processing modules according to a current operation mode of said multimode communication terminal.

14. The method according to claim 9, wherein said channel module comprises:
- an antenna;
- a RF processing module;
- a sample clock; and
- an A/D and D/A converter.

15. The method according to claim 9, wherein said different communication protocols of said first and second channel modules are selected from the group consisting of: a Bluetooth communication protocol, a WLAN communication protocol and a mobile communication protocol.

16. A multimode communication terminal, comprising:
- a first channel module;
- a second channel module, wherein said multimode communication terminal can be configured to communicate by using said first channel module and/or said second channel module, said first and second channel modules communicating according to different communication protocols respectively;
- a channel switch layer means for switching said first channel module to have parameter characteristics consistent with those of said second channel module, such that said multimode communication terminal enables a multiple-input-multiple-output (MIMO) operation mode by using said first channel module and said second channel module at the same time, wherein said MIMO operation mode uses multiple antennas both at a transmitter and a receiver;
- wherein said channel switch layer means comprises a channel module switching means for extracting corresponding parameters from said second channel module, and for configuring at least said first channel module to be switched with said extracted parameters, such that said first channel module and said second channel module enable said multimode communication terminal to perform MIMO communication, wherein said extracted parameters from said second channel module include specific operating state parameters of channel modules and/or signals controlling operating states of the channel modules.

* * * * *